(12) United States Patent
Zhang et al.

(10) Patent No.: US 12,226,104 B2
(45) Date of Patent: Feb. 18, 2025

(54) VALVE CLIP WITH COATINGS AND VALVE CLAMPING SYSTEM

(71) Applicant: HANGZHOU VALGEN MEDTECH CO., LTD., Zhejiang (CN)

(72) Inventors: Tingchao Zhang, Zhejiang (CN); Weiwei Zhang, Zhejiang (CN); Xianzhang Zheng, Zhejiang (CN); Zetao Wang, Zhejiang (CN)

(73) Assignee: HANGZHOU VALGEN MEDTECH CO., LTD., Hangzhou (CN)

( * ) Notice: Subject to any disclaimer, the term of this patent is extended or adjusted under 35 U.S.C. 154(b) by 441 days.

(21) Appl. No.: 17/574,129

(22) Filed: Jan. 12, 2022

(65) Prior Publication Data
US 2022/0133327 A1 May 5, 2022

Related U.S. Application Data

(63) Continuation of application No. PCT/CN2020/105863, filed on Jul. 30, 2020.

(30) Foreign Application Priority Data

Jul. 31, 2019 (CN) .......................... 201910706071.6
Jul. 31, 2019 (CN) .......................... 201921231134.9

(51) Int. Cl.
*A61B 17/122* (2006.01)
*A61B 17/128* (2006.01)
(Continued)

(52) U.S. Cl.
CPC ........ *A61B 17/122* (2013.01); *A61B 17/1285* (2013.01); *A61B 2017/00862* (2013.01); *A61B 2017/00867* (2013.01)

(58) Field of Classification Search
CPC .............. A61B 17/122; A61B 17/1285; A61B 2017/00862; A61B 2017/00867;
(Continued)

(56) References Cited

U.S. PATENT DOCUMENTS

2015/0257877 A1* 9/2015 Hernandez ......... A61B 17/0401
623/2.11
2018/0325671 A1* 11/2018 Abunassar .............. A61F 2/246
(Continued)

FOREIGN PATENT DOCUMENTS

CN    103826548 A    5/2014
CN    106175845 A    12/2016
(Continued)

OTHER PUBLICATIONS

The International Search Report issued in corresponding International Application No. PCT/CN2020/105863, mailed Oct. 27, 2020, 6 pages.
(Continued)

*Primary Examiner* — Kathleen S Holwerda
(74) *Attorney, Agent, or Firm* — HAUPTMAN HAM, LLP

(57) ABSTRACT

The application provides a valve clamping system. The valve clamping system includes a pushing device and a valve clip with coatings. The valve clip includes a push rod, the coatings, and a proximal clamping plate, and a distal clamping plate. The proximal clamping plate and the distal clamping plate extend radially outwardly relative to the push rod. The distal clamping plate is connected to the push rod. The proximal clamping plate is arranged between the push rod and the distal clamping plate. A valve holding space is formed between the proximal clamping plate and the distal clamping plate. The push rod is capable of driving the distal clamping plate to be expanded radially. The proximal clamp-
(Continued)

ing plate is capable of expanding toward the distal clamping plate by an elastic strain of the proximal clamping plate and is configured to clamp a valve tissue received in the valve holding space.

17 Claims, 12 Drawing Sheets

(51) Int. Cl.
*A61F 2/24* (2006.01)
*A61B 17/00* (2006.01)

(58) Field of Classification Search
CPC ............ A61F 2/2466; A61F 2220/0016; A61F 2230/0093; A61F 2/246; A61F 2/24; A61F 2/2463
See application file for complete search history.

(56) References Cited

U.S. PATENT DOCUMENTS

| | | |
|---|---|---|
| 2019/0069991 A1 | 3/2019 | Metchik et al. |
| 2019/0150926 A1 | 5/2019 | Greenberg et al. |

FOREIGN PATENT DOCUMENTS

| | | |
|---|---|---|
| CN | 106491245 A | 3/2017 |
| CN | 107106176 A | 8/2017 |
| CN | 107666868 A | 2/2018 |
| CN | 109717987 A | 5/2019 |
| CN | 109771095 A | 5/2019 |
| CN | 109965921 A | 7/2019 |

OTHER PUBLICATIONS

The Extended European Search Report issued in corresponding EP Application No. EP20846077.4, mailed Oct. 25, 2022, 8 pages.

* cited by examiner

VALVE CLIP WITH COATINGS AND VALVE CLAMPING SYSTEM

CROSS-REFERENCE TO RELATED APPLICATIONS

This application is a continuation of International Application No. PCT/CN2020/105863, filed on Jul. 30, 2020, which claims priority to Chinese Patent Application No. 201910706071.6, filed on Jul. 31, 2019, and Chinese Patent Application No. 201921231134.9, filed on Jul. 31, 2019, the disclosures of which are hereby incorporated by reference in their entireties.

TECHNICAL FIELD

The application relates to the field of medical instruments, in particular to a valve clip with coatings and a valve clamping system.

BACKGROUND

Referring to FIG. 1, a mitral valve 1 is a one-way valve between a left atrium 2 and a left ventricle 3 of the heart. The normal and healthy mitral valve 1 can control blood to flow from the left atrium 2 to the left ventricle 3, while preventing the blood flowing from the left ventricle 3 to the left atrium 2. The mitral valve 1 has a pair of leaflets, called an anterior leaflet 1a and a posterior leaflet 1b. The anterior leaflet 1a and the posterior leaflet 1b are fixed to the papillary muscle of the left ventricle 3 through a chordaetendineae 4. Under normal circumstances, during systole of the left ventricle of the heart, edges of the anterior leaflet 1a and the posterior leaflet 1b are in full coaptation to prevent the blood from flowing from the left ventricle 3 to the left atrium 2. Referring to FIG. 2, when the mitral valve leaflets and associated structures thereof have organic or functional lesion, for example, partial rupture of the chordaetendineae 4, leading to insufficient coaptation of the anterior leaflet 1a and the posterior leaflet 1b of the mitral valve 1. Thus, during systole of the left ventricle 3, the mitral valve 1 cannot close sufficiently. As a result, the blood flows back from the left ventricle 3 to the left atrium 2, causing a series of pathological and physiological changes, which are referred to as "mitral valve regurgitation".

There is a minimally invasive surgery, in which a valve leaflet clamp is delivered to the mitral valve through a delivery device, and then the anterior and posterior leaflets of the mitral valve are simultaneously clamped by relative opening and closing the clamp, so that the anterior and posterior leaflets of the mitral valve are fixed, achieving the purpose of narrowing a leaflet gap and reducing the mitral valve regurgitation. However, in the related art, each of a distal clamping plate and a proximal clamping plate of the clamp is made of metal materials, which may cause tissue allergies or inflammatory reactions. Sharp metal edges may also hurt the valve leaflets by pinching or scratching, resulting in diseases of the mitral valve.

SUMMARY

In view of above, the application provides a valve clip and a valve clamping system which can reduce or avoid damage to the valve tissue.

In order to solve the above technical problem, the application provides a valve clip with coatings. The valve clip includes a push rod, the coatings, and a proximal clamping plate, and a distal clamping plate. The proximal clamping plate and the distal clamping plate extend radially outwardly relative to the push rod. The distal clamping plate is connected to the push rod. The proximal clamping plate is arranged between the push rod and the distal clamping plate. A valve holding space is formed between the proximal clamping plate and the distal clamping plate. The push rod is capable of driving the distal clamping plate to be expanded radially. The proximal clamping plate is capable of expanding toward the distal clamping plate by an elastic strain of the proximal clamping plate and is configured to clamp a valve tissue received in the valve holding space. The coatings include at least one of a first coating or a second coating. The first coating covers at least one side, facing the valve holding space, of the proximal clamping plate. The second coating covers at least one side, facing the valve holding space, of the distal clamping plate.

The application further provides a valve clamping system. The valve clamping system includes a pushing device and the foregoing valve clip. The pushing device includes an operating handle and a pushing component. A proximal end of the pushing component is connected to the operating handle, and a distal end of the pushing component is detachably connected to the valve clip.

In the valve clip and the valve clamping system provided in the application, the coatings are arranged on at least part of surfaces of the proximal clamping plate and/or the distal clamping plate of the valve clip, so as to cover at least part of metal surfaces and/or metal sharp edges of the proximal clamping plate and/or the distal clamping plate, thereby preventing the at least part of metal surfaces and/or metal sharp edges of the valve clip from direct contact with the valve tissue received in the valve holding space, and reducing or avoiding tissue allergies or inflammatory reactions, and avoiding damage to the clamped valve tissue.

BRIEF DESCRIPTION OF THE DRAWINGS

In order to describe the technical solutions in the application more clearly, the accompanying drawings required to be used in the implementations will be simply introduced below. It is apparent that the accompanying drawings in the following descriptions are some implementations of the application. Those of ordinary skill in the art may further obtain other accompanying drawings according to these accompanying drawings without creative work.

DETAILED DESCRIPTION

Figure 1:
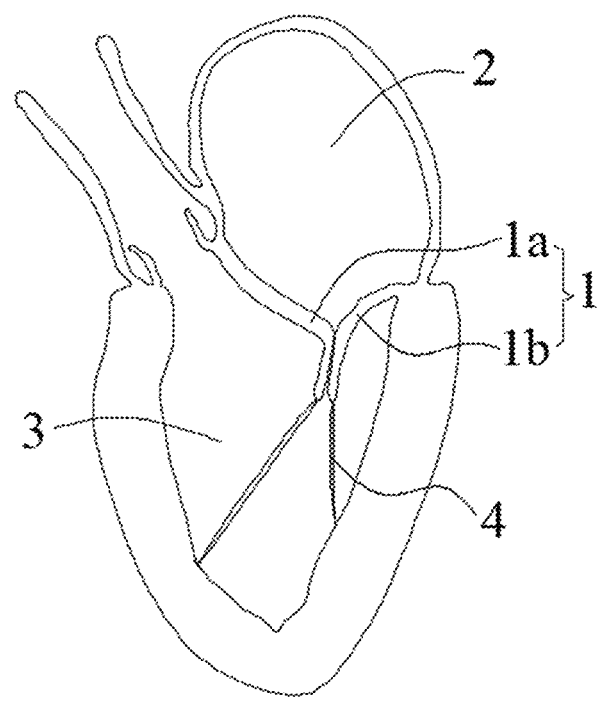
FIG. 1 is a schematic diagram of a mitral valve in a normal state.
Figure 2:
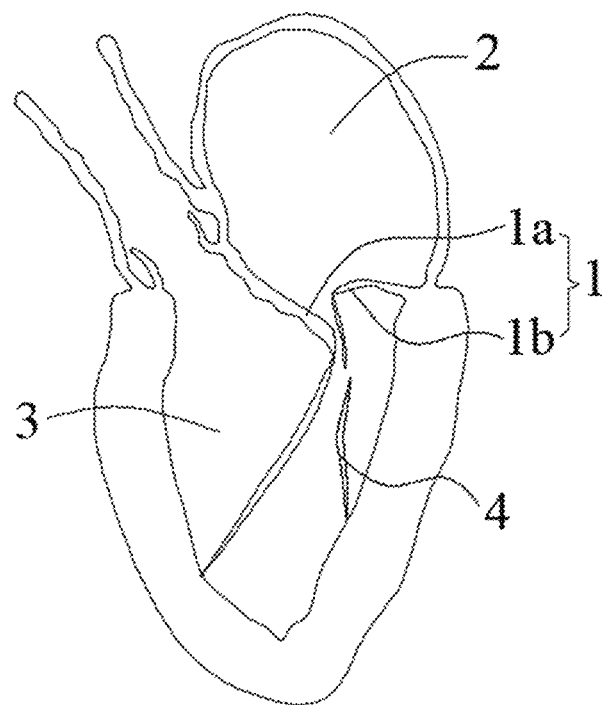
FIG. 2 is a schematic diagram of a mitral valve with a lesion.

The technical solutions in the implementations of the application are clearly and completely described in the following in conjunction with the accompanying drawings of the application. It is apparent that the described implementations are only part of the implementations of the application, not all of the implementations. On the basis of the implementations of the application, all other implementations obtained on the premise of no creative work of those of ordinary skill in the art shall fall within the scope of protection of the application.

In the descriptions of the application, it is to be noted that orientation or position relationships indicated by terms "upper", "down", "left", "right", "inner", "outer" and the like are orientation or position relationships shown in the drawings, are adopted not to indicate or imply that indicated devices or elements must be in specific orientations or structured and operated in specific orientations but only to conveniently describe the application and simplify descriptions and thus should not be understood as limits to the application. In addition, terms "first", "second", "third" and the like are only adopted for description and should not be understood to indicate or imply relative importance.

In the description of the application, it is to be noted that unless otherwise specified and limited, the terms "mounting", "mutual connection", "connection" and the like should be generally understood. For example, the connection may be fixed connection or detachable connection or integral connection, and the connection may be direct connection or indirect connection through an intermediate. Those of ordinary skill in the art may understand specific implications of the above terms in the application in specific situations.

In the description of the application, it is to be noted that in the field of interventional medical instruments, "proximal end" indicates one end close to an operator, "distal end" indicates one end away from the operator, and "axial direction" indicates a direction parallel to a line between a distal center and a proximal center of a medical instrument. The above definitions are only for the convenience of presentation and should not be understood as limits to the application.

Figure 3:
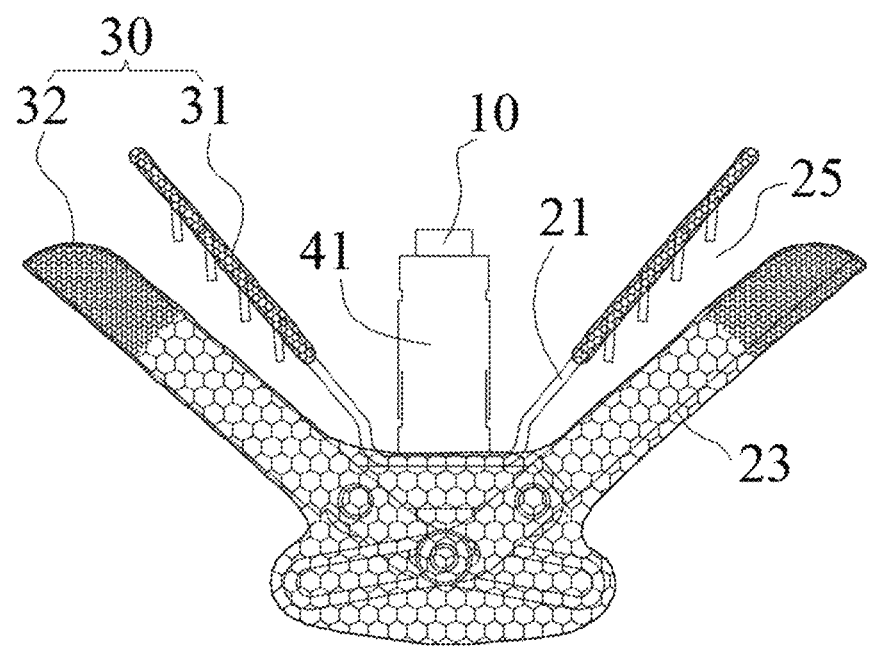
FIG. 3 is a schematic view illustrating a valve clip in an unfolded state according to one implementation of the application.
Figure 4:
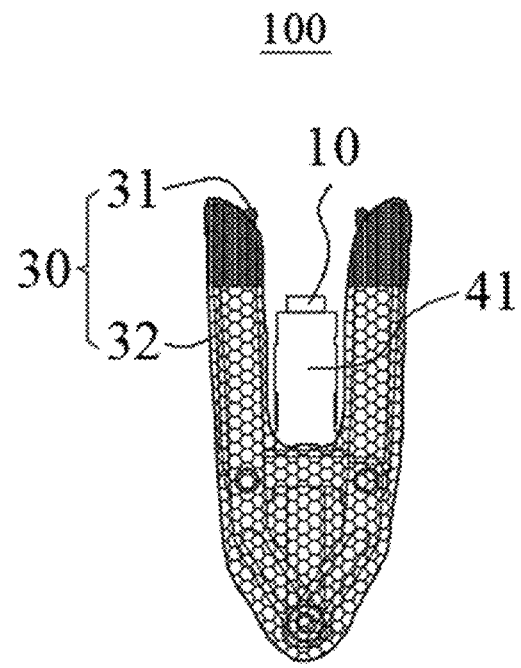
FIG. 4 is schematic view illustrating the valve clip of FIG. 3 in a folded state.
Figure 5:
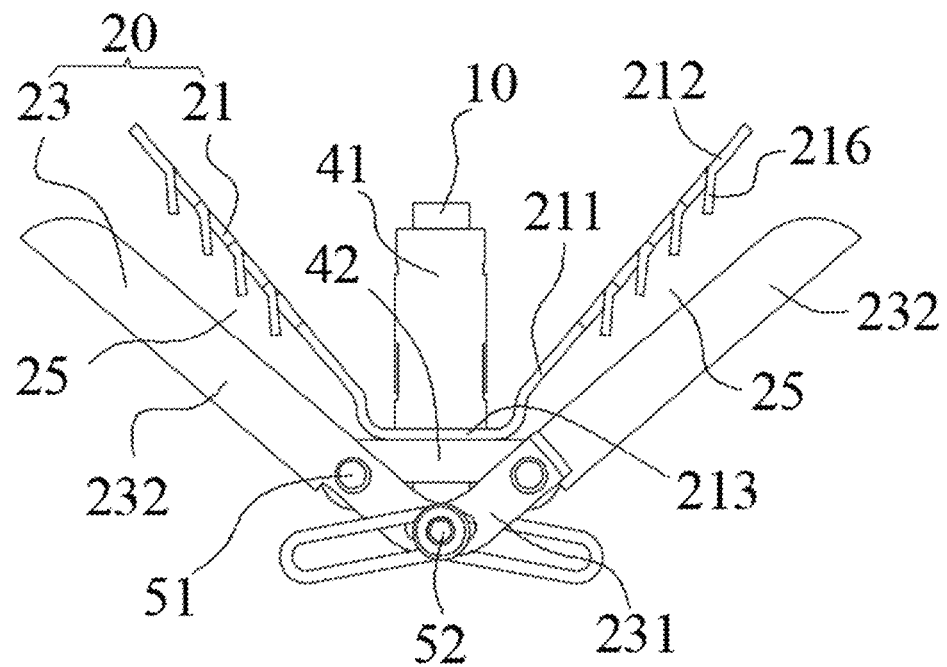
FIG. 5 is a schematic structural view of the valve clip in FIG. 3 before being covered with coatings.

Referring to FIG. 3 to FIG. 5, the application provides a valve clip 100. The valve clip 100 includes a push rod 10 which axially extends, a proximal clamping plate 21, a distal clamping plate 23, and coatings 30. The proximal clamping plate 21 and the distal clamping plate 23 extend radially outwardly relative to the push rod 10. A distal end of the distal clamping plate 23 is connected to the push rod 10. The proximal clamping plate 21 is arranged between the push rod 10 and the distal clamping plate 23. A valve holding space 25 is formed between the proximal clamping plate 21 and the distal clamping plate 23. The push rod 10 is capable of driving the distal clamping plate 23 to be expanded radially. The proximal clamping plate 21 is capable of expanding toward the distal clamping plate 23 by an elastic strain of the proximal clamping plate and is configured to clamp a valve tissue received in the valve holding space 25. The coatings 30 include at least one of a first coating 31 or a second coating 32. The first coating 31 covers at least one side, facing the valve holding space 25, of the proximal clamping plate 21. The second coating 32 covers at least one side, facing the valve holding space 25, of the distal clamping plate 23.

A clamp 20 is composed of one proximal clamping plate 21 and one corresponding distal clamping plate 23.

In order to ensure safety after implantation, each of the proximal clamping plate 21 and the distal clamping plate 23 is made of a biocompatible metal material, which is selected from commonly used metal materials for implantation such as stainless steel, cobalt alloy, cobalt-chromium alloy, titanium alloy, or nickel-titanium alloy. The proximal clamping plate 21 is made of an elastic material having a shape memory function, and the distal clamping plate 23 is made of a rigid material, thereby ensuring that the valve tissue may be fixedly clamped by means of cooperation of the proximal clamping plate 21 and the distal clamping plate 23. In the implementation, the proximal clamping plate 21 is made of hyperelastic nickel-titanium alloy, and the distal clamping plate 23 is made of stainless steel or cobalt-chromium alloy with a high hardness.

Preferably, the first coating 31 extends and covers edges of the proximal clamping plate 21, and the second coating 32 extends and covers edges of the distal clamping plate 23. A coverage rate of the first coating 31 on the proximal clamping plate 21 ranges from 50% to 90%, and a coverage rate of the second coating 32 on the distal clamping plate 23 ranges from 40% to 80%, so that the valve tissue is prevented from being damaged by the edges of the proximal clamping plate 21 and the distal clamping plate 23.

In the application, the first coating 31 and the second coating 32 which are arranged on at least part of surfaces of the proximal clamping plate 21 and/or the distal clamping plate 23 of the clamp 20 can cover at least part of metal surfaces and/or metal sharp edges of the proximal clamping plate 21 and/or the distal clamping plate 23, to prevent the at least part of the metal surfaces and/or the metal sharp edges of the clamp 20 from direct contact with the valve tissue received in the valve holding space 25, thereby reducing or avoiding tissue allergies or inflammatory reactions, and avoiding damage to the clamped valve tissue.

Figure 6:
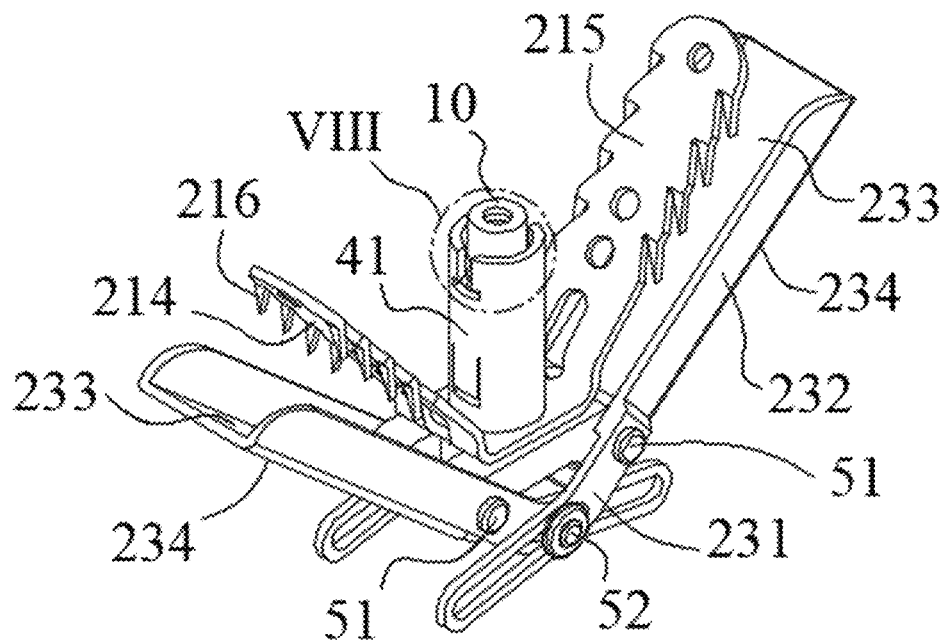
FIG. 6 is a schematic structural view of FIG. 5 in another view.
Figure 7:
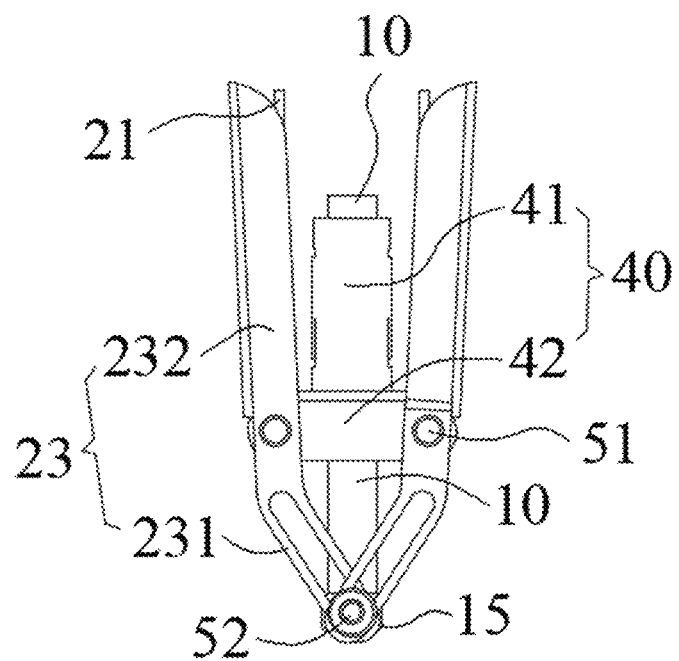
FIG. 7 is a schematic structural view of the valve clip in FIG. 4 before being covered with coatings.
Figure 8:
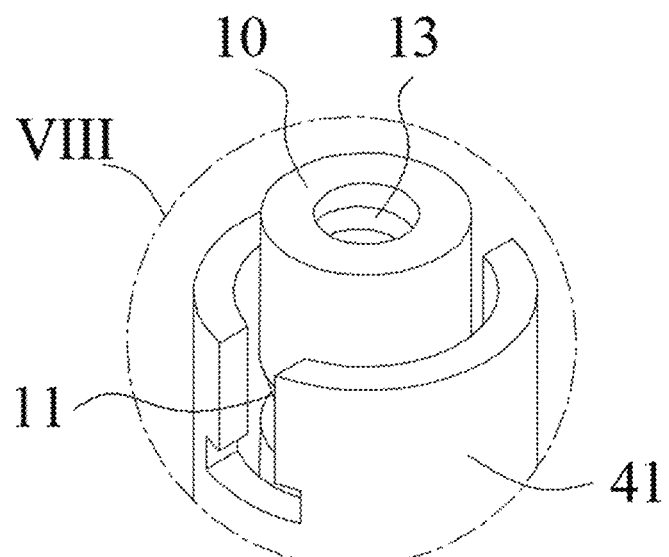
FIG. 8 is an enlarged schematic view of part VIII in FIG. 6.

In an implementation, referring to FIG. 6 to FIG. 8, the push rod 10 is a rod body or a tubular body. In the implementation, the push rod 10 is a round rod body. A circular groove 11 is circumferentially formed at a proximal end of an outer circumference surface of the push rod 10. The push rod 10 defines an internal threaded hole 13 axially extended from a proximal surface of the push rod 10. A connecting base 15 is arranged at a distal end of the push rod 10. The connecting base 15 includes two first planes in opposite and a side surface connecting the two first planes. The two first planes in opposite define through pin holes. The side surface includes a curved surface at the distal end and a second plane that is located at the proximal end and connected to the curved surface. The distal end of the push rod 10 is perpendicularly fixed on the second plane. The area of the second plane is greater than the cross section area of the push rod 10. Sizes of cross sections, parallel to the second plane, of the connecting base 15 are gradually decreased from the distal end to the proximal end. In other words, the connecting base 15 may be a structure shaped as a semi-sphere, a spherical crown, or a bullet, so that the valve clip 100 may be pushed in the human body more easily.

Each of the push rod 10 and the connecting base 15 has a smooth outer surface to avoid damaging the leaflets or hooking the chordaetendineae.

Each of the push rod 10 and the connecting base 15 is made of a biocompatible material such as stainless steel, cobalt alloy, cobalt-chromium alloy, or titanium alloy. Preferably, each of the push rod 10 and the connecting base 15 is made of stainless steel, or cobalt-chromium alloy.

Figure 9:
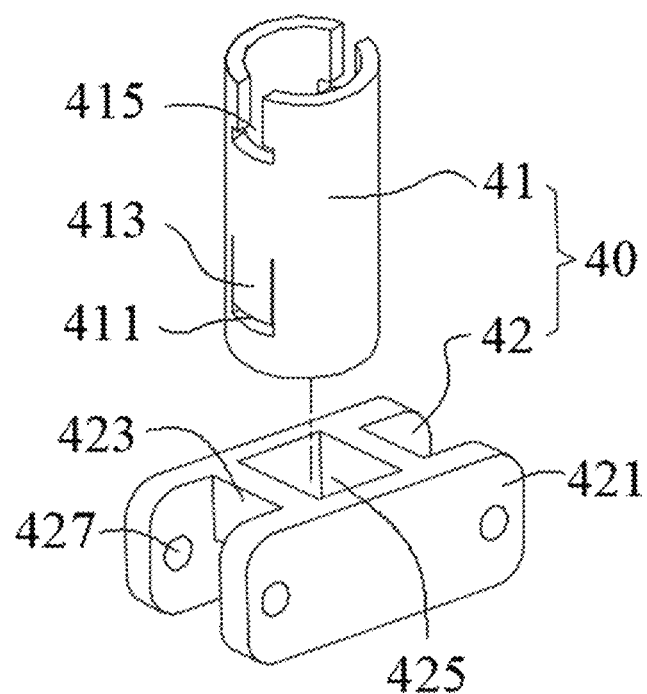
FIG. 9 is an explored view of a fixing base in FIG. 6.

Further, referring to FIG. 6, FIG. 7, and FIG. 9, the valve clip 100 further includes a fixing base 40. The fixing base 40 includes a first base body 41 and a second base body 42 connected to a distal end of the first base body 41. The first base body 41 and the second base body 42 may be integrally or non-integrally formed. In the implementation, the first base body 41 and the second base body 42 are integrally formed.

In the implementation, the first base body 41 is a circular tube open at both ends. The push rod 10 is arranged in a tube cavity of the first base body 41. An opening 411 is formed in an outer wall, close to a distal end, of the first base body 41. An elastic piece 413 is arranged in the opening 411 and includes a connecting end and a free end opposite to the connecting end. The connecting end is connected to a proximal edge of the opening 411. The free end extends to the inner cavity of the circular tube. That is, in a natural state, the free end of the elastic piece 413 is inclined to the tube cavity of the first base body 41, relative to the connecting end. A connecting part 415 is arranged at a proximal end of the first base body 41 and used to be connected to a pushing device that pushes the valve clip 100 to the cardiac valve. In the implementation, the connecting part 415 defines at least a pair of T-shaped grooves on the outer wall of the first base body 41. Preferably, the at least a pair of T-shaped grooves are in symmetrical arrangement around an axis of the first base body 41. Each T-shaped groove includes a first groove section and a second groove section perpendicularly crossed with the first groove section. The second groove section is disposed at a distal end of the first groove section. An extension direction of the first groove section is the same as an axial direction of the first base body 41. A proximal end of the first groove section penetrates a proximal surface of the first base body 41.

In the implementation, the second base body 42 includes two clamp plates 421 at an opposite interval. The two clamp plates 421 are connected via two connecting rods 423. The two connecting rods 423 are arranged at an interval. The two connecting rods 423 and the two clamp plates 421 encircle to form a threading passage 425 that corresponds to the tube cavity of the first base body 41. The push rod 10 may be inserted in the threading passage 425 and the tube cavity of the first base body 41, and can axially move therein. Further, fixing holes 427 are formed at two opposite ends of the two clamp plates 421.

The threading passage 425 may be a square passage or a circular passage. In the implementation, the threading passage 425 is a square passage.

It can be understood that, only one implementation of the fixing base 40 is provided. Actually, the fixing base 40 may be of other structures, which will not be elaborated herein.

Figure 10:
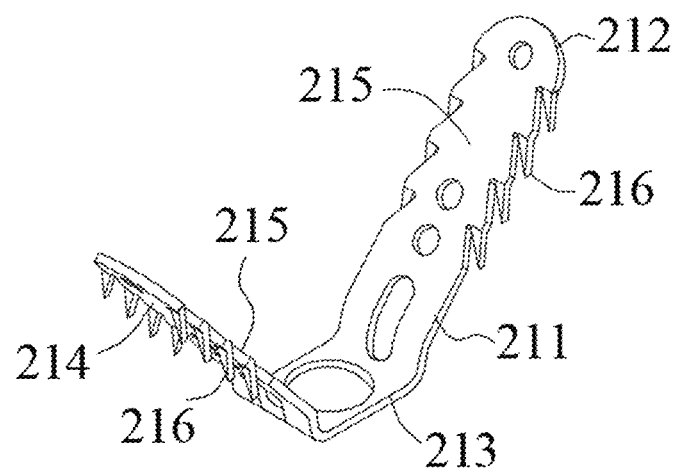
FIG. 10 is a schematic structural view of a proximal clamping plate in FIG. 6.

Referring to FIG. 5 and FIG. 10, the proximal clamping plate 21 includes a connecting end 211 and a free end 212 opposite to the connecting end 211. The connecting end 211 is fixed to the fixing base 40. In the implementation, the connecting ends 211 of the two proximal clamping plates 21 are integrally connected through a connecting piece 213. The connecting piece 213 defines a through hole therein. The middle of the connecting piece 213 is fixedly connected to a joint of the first base body 41 and the second base body 42, so that the connecting ends 211 of the two proximal clamping plate 21 are fixed to the fixing base 40. The through hole of the connecting piece 213 corresponds to the inner cavity of the first base body 41. It is noted that, in other implementations, the connecting ends 211 of the proximal clamping plate 21 may be directly fixed to the joint of the first base body 41 and the second base body 42.

At least part of the proximal clamping plate 21 is made of an elastic material having a shape memory function. Through heat setting, in a natural state, the proximal clamping plate 21 form an expanded U-shape. That is, the proximal clamping plate 21 and the push rod 10 are arranged at an angle, thereby facilitating cooperation between the proximal clamping plate 21 and the distal clamping plate 23 to clip the valve tissue. An angle between two extension sides of the integral proximal clamping plates 21 ranges from 0 to 200 degrees. In the implementation, the proximal clamping plate 21 is prepared as follows. Nickel-titanium alloy is first cut and placed in a setting mold, the setting mold with the Nickel-titanium alloy cut is then placed in an electric-heating circulating-air box-type furnace, heat setting is performed under 300-650° C., the Nickel-titanium alloy is then taken out of the furnace to cool in purified water rapidly, and the setting mold is finally removed to obtain the shaped proximal clamping plates 21. In the implementation, the proximal clamping plate 21 is integrally made of the nickel-titanium alloy, so that an elastic force is provided to drive the proximal clamping plate 21 to move toward the distal clamping plate 23 when clamping the valve tissue. In other implementations, the connecting ends 211 of the proximal clamping plate 21 are made of an elastic material, the free ends 212 of the proximal clamping plate 21 are made of a non-elastic material such as aluminum alloy. The proximal clamping plate 21 can be driven by the elastic force of the connecting ends 211 to be close to the distal clamping plate 23.

It is to be noted that the free ends 212, extending radially outwardly toward the distal end relative to the push rod 10, of the proximal clamping plate 21 may be controlled through an adjusting wire. In a delivery state, the free ends 212 of the proximal clamping plate 21 are tightened by the adjusting wire to be in contact with the surface of the fixing base 40 and adjacent to the push rod 10. When the free ends 212 tightened are released by the adjusting wire, the connecting ends 211 of the proximal clamping plate 21 rebound due to their elastic memory performances, and the proximal clamping plate 21 restore to the natural state to push the valve to the distal clamping plate 23. In an implementation, the angle between the two extension sides of the proximal clamping plate 21 in a natural expanded state should be slightly greater than an angle between the two distal clamping plates 23, such that a stable clamping force is provided. That is, an angle between each extension side of the proximal clamping plate 21 in the natural expanded state and the push rod 10 is greater than or equal to an angle between the distal clamping plate 23, corresponding to the extension side and opening to the utmost extent, and the push rod 10, it is ensured that a certain clamping force can be applied by the distal clamping plate 23 and the proximal clamping plate 21 to clamp the valve tissue between the distal clamping plate 23 and the proximal clamping plate 21.

Further, the proximal clamping plate 21 also includes a first surface 214 facing the distal clamping plate 23 and the valve holding space 25 and a second surface 215 opposing the first surface 214. The first surface 214 is provided with clamp reinforcers 216 to increase a friction force between the proximal clamping plate 21 and the valve tissue clamped in the valve holding space 25, thereby improving a clamping force applied on the valve tissue by the valve clip 100. In the implementation, each clamp reinforcer 216 refers to two rows of barbs which are spaced apart and arranged at two opposite sides of each first surface 214. The barbs may be integrally formed with the proximal clamping plate 21. Alternatively, the barbs may be first formed by a material the same with or different from that of the proximal clamping plate 21 and then be connected to the first surface 214 of the proximal clamping plate 21. For example, the barbs may be nickel-titanium metal wires or nickel-titanium metal rods which are fixed on the first surface 214 through sleeves. Roots of the barbs are connected to the proximal clamping plate 21. Ends, opposite to the roots, of the barbs, are free ends. In the natural expanded state, the free ends of the barbs face the distal clamping plate 23. An angle between an extension direction of each barb and an extension direction of the first surface 214 is less than or equal to 90 degrees, so that a clamping force of the valve clip 100 to the valve tissue is enhanced. Further, the free end of each barb has a smooth curved surface to avoid damaging the valve tissue.

In other implementations, the number of the barbs may be one, two, or other reasonable number.

In other implementations, the clamp reinforcers 216 may be structures such as ribs, bosses, or other irregularly distributed protrusions protrusively arranged on the first surface 214. Alternatively, the clamp reinforcers 216 may be rough surfaces at least partially covering the first surface 214, so as to improve the clamping force applied to the valve tissue.

The proximal clamping plate 21 is provided with multiple holes to reduce its weight, thereby preventing the clamp 10 hanging below the leaflets for a long time from slipping or damaging the leaflets, and further, being conductive to climbing and growth of endothelial cells.

Referring to FIG. 5 to FIG. 7, the valve clip 100 includes two distal clamping plates 23 which are arranged in axial symmetry relative to the push rod 10. The distal clamping plate 23 includes a connecting section 231 at a distal end thereof and a clamping section 232 arranged at a proximal end of the connecting section 231. The proximal end of the connecting section 231 is rotationally connected to the second base body 42 of the fixing base 40. The distal end of the connecting section 231 is movably connected to the connecting base 15 of the push rod 10. In the implementation, the distal clamping plate 23 is rotationally connected to the second base body 42 of the fixing base 40 through a first pin 51. The two distal clamping plates 23 are arranged at two opposite ends of the first base body 42, and distal ends of the two distal clamping plate 23 are intersected and are movably connected to the connecting base 15 of the push rod 10 through a second pin 52.

In other implementations, the first pin 51 and/or the second pin 52 may be replaced with a bolt.

In the implementation, the connecting section 231 of the distal clamping plate 23 includes two connecting pieces spaced apart. Each connecting piece defines a connecting hole at a proximal end thereof and a slide slot at a distal end thereof. The slide slot extends along a direction from the distal end of the connecting piece to the proximal end of the connecting piece. Apparently, in other implementations, the connecting section 231 may include only one connecting piece.

In an implementation, one end of the first pin 51 first penetrates the connecting hole of the connecting piece at one side of the distal clamping plate 23, then penetrates the fixing holes 427 of the second base body 42, and finally is inserted in the connecting hole of the connecting piece at the opposite side of the distal clamping plate 23. A first stopper is welded to an end of the first pin 51 to prevent the first pin 51 from slipping. As such, the proximal end of the connecting section 231 of the distal clamping plate 23 is rotationally connected to the second base body 42 of the fixing base 40. The connecting sections 231, on the same side of the second base body 42, of the two distal clamping plate 23 overlap mutually, and the slide slots of the two connecting sections 231 are in communication. One end of the second pin 52 sequentially penetrates the slide slots of the two connecting pieces, on the same side of the connecting base 15, of the two distal clamping plate 23, then penetrates a pin hole on the connecting base 15, and finally is inserted in the slide slots of the two connecting pieces, on the opposite side of the connecting base 15, of the two distal clamping plate 23. A second stopper is welded to an end of the second pin 52 to prevent the second pin 52 from slipping. As such, distal ends of the connecting sections 231 of the two distal clamping plate 23 are movably connected to the connecting base 15 of the push rod 10 via the same second pin 52.

When the push rod 10 axially moves in the threading passage 425 and the tube cavity of the first base body 41, the second pin 52 penetrating the pin holes of the connecting base 15 can slide in the slide slots of the connecting pieces of the distal clamping plate 23, to drive the distal clamping plate 23 to rotate around the first pin 51 by taking a jointed position where the distal end of the connecting section 231 is connected to the second base body 42 as a rotation center. The clamping sections 232 of the distal clamping plate 23 are unfolded and folded relative to the fixing base 40 and the push rod 10. When being released, the proximal clamping plate 21 is freely unfolded due to their elastic memory function to move toward the distal clamping plate 23 to clamp the valve tissue.

Further, the distal clamping plate 23 also includes a third surface 233 facing one proximal clamping plate 21 and the valve holding space 25, and a fourth surface 234 opposing the third surface 233. The third surface 233 is opposite to the first surface 214 of the proximal clamping plate 21.

The third surface 233 may be a plane or a curved surface. In the implementation, the third surface 233 is a curved surface, a curvature direction of the curved surface faces the proximal clamping plate 21. Since the third surface 233 is configured as a curved surface, a contact area between the distal clamping plate 23 and the valve tissue and a clamping area of the distal clamping plate 23 may be expanded, thereby providing a stable clamping force. In addition, the third surface 233, which is a curve surface, may define an accommodating grooves. When the proximal clamping plate 21 is moved toward the distal clamping plate 23, the barbs on the first surface 214 of the proximal clamping plate 21 can be accommodated in the accommodating grooves, so as to compact the leaflets in the valve holding space 25, or minimize the size of the valve clip 100 when being folded, so that the valve clip 100 may be delivered in the body more easily.

A clamp reinforcing structure may be arranged on the third surface 233. The clamp reinforcing structure may be a protrusion, a groove, or a pad which is made of a biocompatible material with high friction coefficient and attached on the third surface 233. The protrusion, the groove, or the pad arranged on the third surface 233 can increase a friction force between the distal clamping plate 23 and the valve tissue, thereby providing a stable clamping force.

Referring to FIG. 3 and FIG. 6, in the application, in order to prevent the metal surfaces and/or the metal sharp edges of the valve clip 100 from damaging the clamped valve tissue, the valve clip 100 is covered with the coatings 30. In the implementation, the coatings 30 include the first coating 31 that covers the proximal clamping plate 21 and/or the second coating 32 that covers the distal clamping plate 23.

The first coating 31 at least covers the entire first surface 214 of the proximal clamping plate 21, the second coating 32 at least covers the entire third surface 233 of the distal clamping plate 23. Preferably, in the implementation, the first coating 31 covers the entire first surface 214 and extends to cover the entire second surface 215. The second coating 32 covers the entire third surface 233 and extends to cover the entire fourth surface 234. In an implementation, the first coating 31 at least partially covers the first surface 214 of the proximal clamping plate 21. The second coating 32 at least partially covers the third surface 233 of the distal clamping plate 23.

In other implementations, the first coating 31 may extend to partially cover the second surface 215. The second coating 32 may extend to partially cover the fourth surface 234. As such, use of the coating is reduced while cost is lowered.

Each of the first coating 31 and the second coating 32 is made of at least one layer of polymer material which is biocompatible, antioxidative, and resists dissolving. The polymer material is selected from at least one of polyethylene terephthalate (PET), polyester, poly tetra fluoro ethylene (PTFE), silicon resin, silica gel, or urethane. Further, the first coating 31 and the second coating 32 may be made of the same or different materials. In the implementation, the first coating 31 and the second coating 32 are both preferably single-layer PET coatings.

The first coating 31 and the second coating 32 are fixed by any one of methods such as stitching, dip-coating, bonding, fusion, or binding. In the implementation, the first coating 31 is fixed to the proximal clamping plate 21 by adhering, and the second coating 32 is fixed to the distal clamping plate 23 by stitching.

In the implementation, two surfaces and edges thereof, facing the valve holding space 25, of the valve clip 100 are fully covered with the coatings 30, the valve tissue received in the valve holding space 25 will not in direct contact with metal parts of the clamp 20, so that tissue allergy, inflammatory reaction, pinching or scratching of the valve tissue received in the valve holding space 25 may be avoided.

In other implementations, the valve clip 100 may be covered with the first coating 31 or the second coating 32. That is, one side surface and edges thereof, facing the valve holding space 25, of the valve clip 100, are fully covered with the coatings 30. In an implementation, the first coating 31 covers the side surface, facing the valve holding space 25, of the proximal clamping plate 21, alternatively, the second coating 32 covers the side surface, facing the valve holding space 25, of the distal clamping plate 23. In this way, it may also reduce damage to the valve tissue.

As shown in FIG. 3 and FIG. 4, in the implementation, the second coating 32 covering the two distal clamping plates 23 together covers an outer surface of a jointed part (i.e., a part where the connecting base 15 of the second base body 42 and the push rod 10 is located) of the two distal clamping plate 23, so that metal sharp edges of the jointed part are fully covered to avoid damaging the valve tissue or blood vessel inner walls during pushing of the valve clip 100.

In the other implementations, the jointed part may not be covered with the second coating 32.

Further, the coatings 30 are provided with functional drugs through treatment methods such as biological modification, dipping, brushing, dripping, or spraying. For example, the surfaces of the first coating 31 are applied with an anticoagulant such as heparin by dipping, spraying. Alternatively, the surfaces of the first coating 31 may be biologically modified to have properties of antithrombin. In addition, the first coating 31 may also be applied with a drug coating containing at least one of anticoagulant drugs, antiplatelet drugs, or anti-tissue proliferation drugs, thereby promoting endothelialization, avoiding excessive tissue proliferation, reducing incidence of corresponding complications, and increasing a postoperative survival rate. Similarly, the second coating 32 may be provided with corresponding functional drugs, which will not be elaborated herein.

Figure 11:
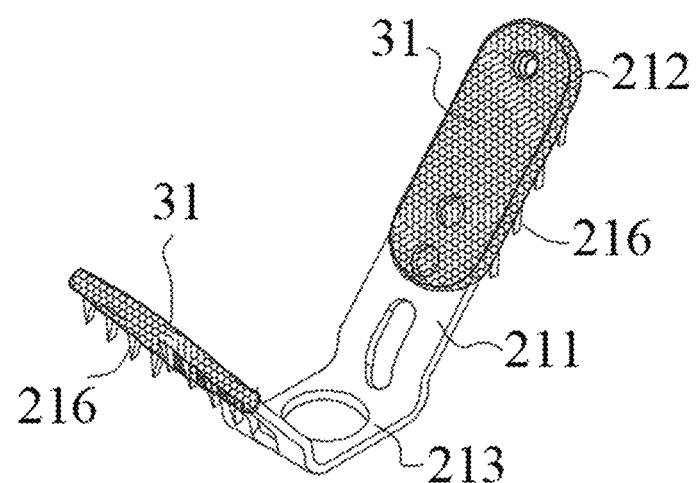
FIG. 11 is a schematic view of the proximal clamping plate, in FIG. 10, covered with a first coating.

Referring to FIG. 11, after the proximal clamping plate 21 is covered with the first coating 31, the free ends of the barbs 216 penetrate out of the first coating 31 to facilitate clamping of the valve tissue. Preferably, a thickness of a region of the first coating 31 close to the barbs 216 is greater than a thickness of other regions of the first coating 31 covering the proximal clamping plate 21, so as to prevent the damage to the valve tissue caused by the free ends of the barbs 216 penetrating the first coating 31 too long and piercing the valve tissue deeply.

The free end of the barbs penetrates out of the first coating 31 by a length ranging from 0.2 mm to 2 mm, and preferably 0.5 mm to 1 mm.

Figure 12:
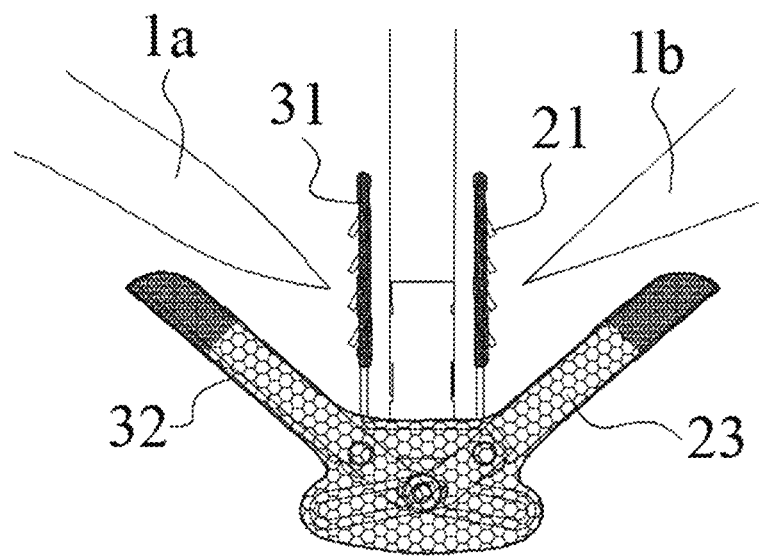
FIG. 12 is a schematic view illustrating that the distal clamping plate of the valve clip in FIG. 3 is supported below leaflets.
Figure 13:
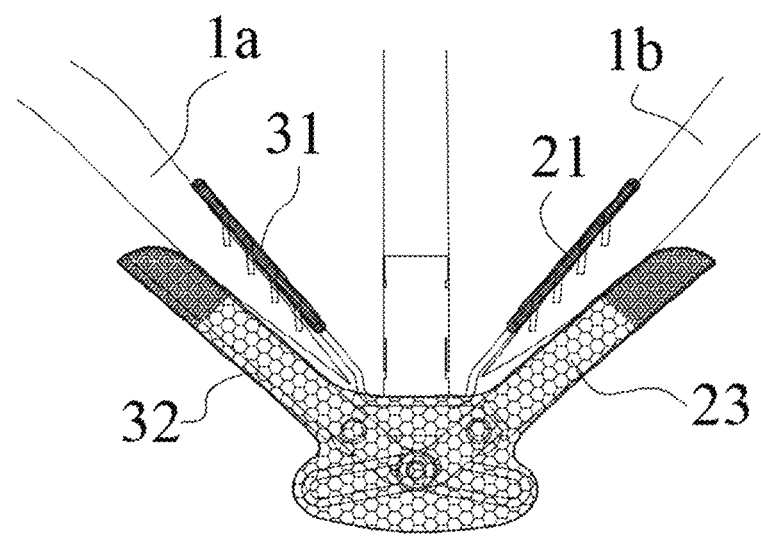
FIG. 13 is a schematic view illustrating that the proximal clamping plate of the valve clip in FIG. 3 is close to the distal clamping plate to clamp a valve.

It can be understood that when the proximal clamping plate 21 is not covered with the first coating 31, the metal sharp edges caused by machining are all exposed, and more exposed sharp edges are likely to cause damage to the valve tissue. Referring to FIG. 12 and FIG. 13, in the application, after the proximal clamping plate 21 is covered with the first coating 31, most metal sharp edges are covered by the first coating 31, only the free ends of the barbs are exposed, so that the clamping force to the valve tissue can be ensured while severe damage to the valve tissue may be avoided. Further, when the valve tissue is clamped with the barbs 216, the first coating 31 as a whole may have a certain blocking and controlling effect to penetration of the barbs 216, so that the penetration depth of the barbs 216 into the valve tissue may be effectively controlled to reduce excessive damage to the valve caused by unbalanced stress. In addition, in some extreme conditions, once the valve is pierced by the barbs 216, the first coating 31 may immediately cover the pierced site. With the highly-biocompatible polymer material of the first coating 31 and under action of the functional drugs on the first coating 31, the growth of tissue near the pierced site may be promoted, thereby quickly blocking the pierced hole, preventing the blood from permeating the pericardial cavity, and reducing the risk of pericardial effusion and even cardiac arrest.

Similarly, when the distal clamping plate 23 is covered with the second coating 32, most of the metal surfaces of the distal clamping plate 23 are covered by the second coating 32, so that the distal clamping plate 23 is prevented from causing serious damage to the valve tissue.

In addition, the first coating 31 and the second coating 32 may also play a buffering effect, so that the clamped valve tissue is evenly stressed, and damage to the valve tissue caused by excessive local force is avoided.

Figure 14:
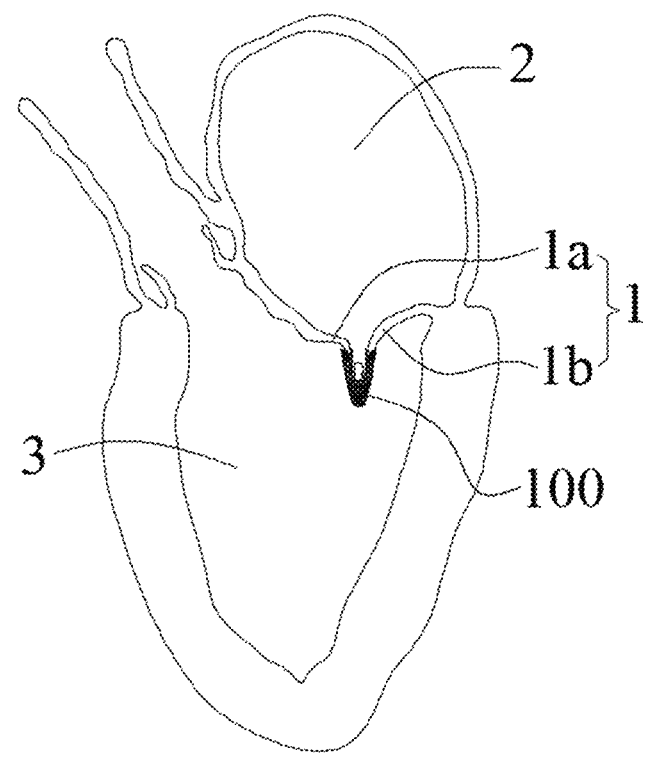
FIG. 14 is a schematic diagram illustrating a position of the valve clip in FIG. 3 when in use.
Figure 15:
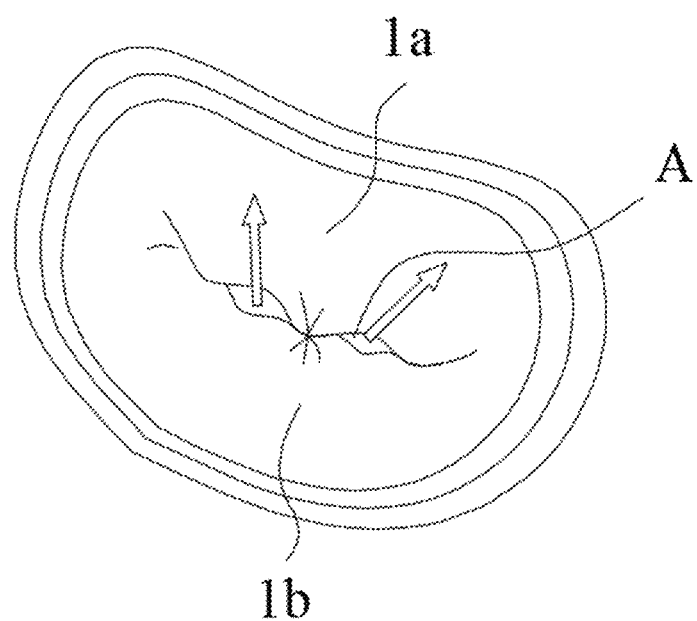
FIG. 15 is a schematic diagram illustrating the mitral valve during systole when the leaflets are clamped by the valve clip in FIG. 14.
Figure 16:
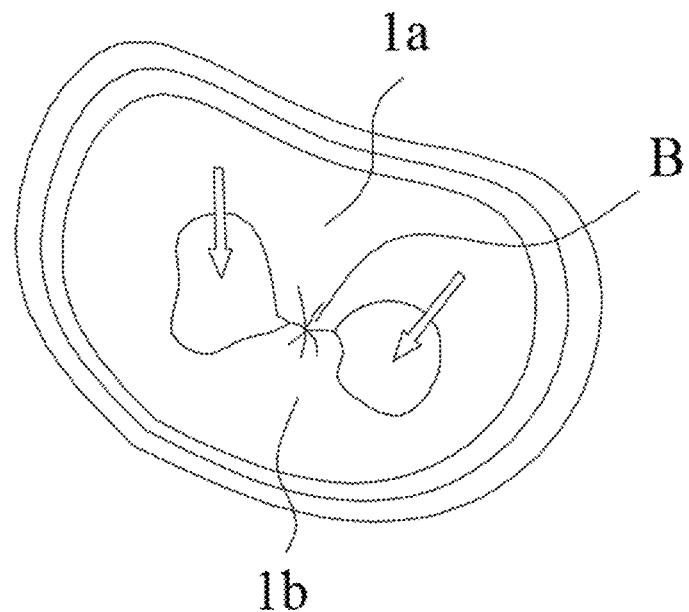
FIG. 16 is a schematic diagram illustrating the mitral valve during diastole when the leaflets are clamped by the valve clip in FIG. 14.

As mentioned above, in this implementation, the valve clip 100 can be used to reduce or treat "mitral valve regurgitation". In an implementation, referring to FIG. 14 to FIG. 16, the valve clip 100 is placed at the position where the anterior leaflet 1a and the posterior leaflet 1b of the mitral valve cannot achieve coaptation properly, one side of one distal clamping plate 23 and one side of one proximal clamping plate 21 clamp an edge of the anterior leaflet 1a of the mitral valve, and one side of the other distal clamping plate 23 and one side of the other proximal clamping plate 21 clamp an edge of the posterior leaflet 1b of the mitral valve, so that the anterior leaflet 1a and the posterior leaflet 1b of the mitral valve are clamped together at the positions where they cannot achieve coaptation properly. The coatings 30 on the valve clip 100 can prevent the mitral valve from being pinched or scratched. As shown in FIG. 15, during systole, the anterior leaflet 1a and the posterior leaflet 1b are contracted, and the positions where the anterior leaflet 1a and the posterior leaflet 1b cannot achieve coaptation properly is partially or completely contracted together. The opening area A of the mitral valve is reduced or the mitral valve can be completely closed, only a small amount of blood flows back from the opening of the mitral valve into the left atrium, which can reduce or treat the "mitral valve regurgitation". As shown in FIG. 16, during diastole, the anterior leaflet 1a and the posterior leaflet 1b achieve coapation only at position B clamped by the valve clip 100, and the other positions of the anterior leaflet 1a and the posterior leaflet 1b are still in normal diastole. This allows blood to enter the left ventricle from the left atrium, thereby ensuring normal circulation of blood.

An arrow direction shown in FIG. 15 and FIG. 16 is a blood flow direction.

The coatings 30 may allow or stop blood to permeate. Preferably, in this implementation, the first coating 31 and the second coating 32 may allow blood to permeate to increase a blocking force during blood circulation, thereby reducing a blood pressure difference between the left atrium and the left ventricle.

In an implementation, referring to FIG. 3 and FIG. 4, each of the coatings 30 is at least one of a two-dimensional sieve structure, a porous membrane, a micro-pore structure, a woven mesh structure, a non-woven mesh structure, or a foaming structure. Therefore, the blood can permeate the coatings 30 for circulation. In this implementation, the first coating 31 and the second coating 32 both adopt a woven mesh structure, and both have multiple meshes.

A porosity of the first coating 31 is less than a porosity of the second coating 32.

The porosity refers to a percentage of an open area to the entire coating area.

The porosity of the second coating 32 is relatively large, so that the second coating 32 has better elasticity and ductility than the first coating 31. When the distal clamping plate 23 covered with the second coating 32 is unfolded or folded relative to the push rod 10, the second coating 32 can elastically deform along the unfolding and folding of the distal clamping plate 23, and the second coating 32 is always attached to the distal clamping plate 23.

The number of meshes per inch of the first coating 31 ranges from 250 to 2500, and the number of meshes per inch of the second coating 32 ranges from 24 and 250. In this implementation, the number of meshes per inch of the first coating 31 is preferably 500 to 2500, and the number of meshes per inch of the second coating 32 is preferably 50 to 150.

The meshes on the first coating 31 and the second coating 32 may allow blood to pass through but prevent blood clots from passing through. Further, a diameter of each mesh of the first coating 31 is less than that of each mesh of the second coating 32. In an implementation, the diameter of the mesh of the first coating 31 ranges from 0.01 mm to 0.1 mm, and the diameter of the mesh of the second coating 32 ranges from 0.2 mm to 0.5 mm. In this implementation, the diameter of the mesh of the first coating 31 is preferably 0.01 mm to 0.05 mm, and the diameter the mesh of the second coating 32 is preferably 0.2 mm to 0.5 mm.

Preferably, in some implementations, the diameters of the meshes arranged, along a direction from the proximal end to the distal end of the distal clamping plate 23, of the second coating 32 are gradually increased. That is, mesh compactness of the second coating 32 covering a proximal region (i.e., the clamping section 232) of the distal clamping plate 23 is higher than that of the second coating 32 covering a distal region (i.e., the connecting section 231) of the distal clamping plate 23.

In an implementation, as shown in FIG. 3 and FIG. 4, in this implementation, since the mesh of the second coating 32 covering the proximal region (i.e., the clamping section 232) of the distal clamping plate 23 has a relatively diameter, the second coating 32 on the proximal region has high compactness, and accordingly is not easy to be worn out by proximal edges of the distal clamping plate 23 and may not affect folding and unfolding of the distal clamping plate 23. Since the mesh of the second coating 32 covering the distal region (i.e., the connecting section 231) of the distal clamping plate 23 has a relatively diameter, the second coating 32 on the distal region has excellent elasticity and ductility, even in case of that the clamp 20 has a large opening angle, the second coating 32 close to the push rod 10 can transform correspondingly along with the folding and unfolding of the distal clamping plate 23, thereby ensuring that the second coating 32 to fit and be fixed to the distal clamping plate 23.

In the application, the first coating 31 is provided with multiple meshes, so that the first coating 31 can allow blood to permeate without affecting the normal flow of blood from the left atrium to the left ventricle, and avoiding blood stagnation in the left atrium, thereby reducing damage caused by blood pressure to the left atrial cavity. Moreover, the number and diameter of the meshes of the first coating 31 are set reasonably, the first coating 31 can also form an artificial barrier on the atrial side of the valve leaflets to block blood clots, close an opening of the whole valve clip 100 facing the atrium to prevent the blood clots from entering the inside of the valve clamp 100 or the left ventricle, thereby preventing the valve clip 100 from falling off or the blood clots entering the left ventricle from the left atrium and then passing through the aorta to enter the blood circulation of the human body. In addition, since the first coating 31 prevents the blood clots from entering between the first coating 31 and the distal clamping plate 23, the impact force of the blood clots on the distal clamping plate 23 is reduced, service lives of the end clamping plates 23 is prolonged, and further the service life of the valve clip 100 is prolonged. Moreover, the first coating 31 can also increase the contact area between the proximal clamping plate 21 and the blood to buffer the inflowing blood, so as to avoid the inflowing blood impacting the valve clip 100 as much as possible, to prevent the proximal clamping plate 21 deforming to slip off.

Similarly, in the application, the second coating 32 with the multiple meshes may make blood flow normally between the left atrium and the left ventricle, thereby reducing a blood pressure difference between the left atrium and the left ventricle. Furthermore, the second coating 32 can also block a very small amount of blood clots that enter the valve clip 100 through the first coating 31 and remain them in the valve clip 100, thereby preventing the blood clots from entering the left ventricle or entering the human blood circulation to induce stroke.

It is to be noted that static friction refers to two objects that are in contact with each other. When there is a tendency for relative sliding between contact surfaces of the two objects, but the two objects are still relatively static, they act on each other to hinder relative sliding resistance. This resistance is called static sliding friction, referred to as static friction for short, is generally denoted by F. A magnitude of the static friction may vary between 0 and FMAX, where FMAX is the maximum static friction, which is approximately equal to the sliding friction f. The magnitude of the sliding friction force f is proportional to the positive pressure N, that is, $f=\mu N$. $\mu$ is a dynamic friction factor, which is related to the material, roughness of the contact surface and the elastic force between the contact surfaces. For the valve clip 100 implanted on the valve leaflet, the first surface 214, facing of the distal clamping plate 23, of the proximal clamping plate 21 is in contact with upper surfaces of the valve leaflets. The third surface 233, facing the proximal clamping plate 21, of the distal clamping plate 23 is in contact with lower surfaces of the leaflets. Because the leaflet tissue is sticky and slippery, the surface thereof is filled with blood in constant high-speed motion, there is always a tendency of relative sliding between the first surface 214 of the proximal clamping plate 21 and the upper surfaces of the leaflets, as well as between the third surfaces 233 of the distal clamping plate 23 and the lower surfaces of the leaflets. In the related art, in order to avoid sliding or even slipping off between the clamps and the leaflets, only methods such as adding barbs and friction pads or simply increasing the contact area of the valve leaflets are adopted to avoid sliding. However, in this implementation, the proximal clamping plate 21 having an elastic memory function is covered with the first coating 31 with high density and small porosity, the distal clamping plate 23 made of the rigid material is covered with the second coating 32 with a relatively low density and large porosity. When the valve clip 100 is affected by the blood flow erosion and the flapping of the valve leaflets, and a positive pressure N is unchanged, the dynamic friction factor $\mu$ between the first surface 214 of the proximal clamping plate 21 and the upper surfaces of the leaflets, as well as between the third surfaces 233 of the distal clamping plate 23 and the lower surfaces of the leaflets is increased, so that two friction forces are respectively increased, and match mutually to achieve a dynamic balance in a stressed state, and the clamping force and the stability of the valve clip 100 are further improved.

Figure 17:
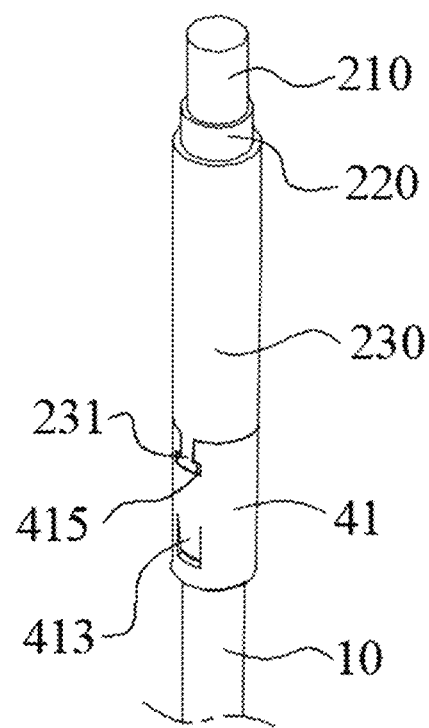
FIG. 17 is a partial schematic structural view of a valve clamping system according to an implementation of the application.
Figure 18:
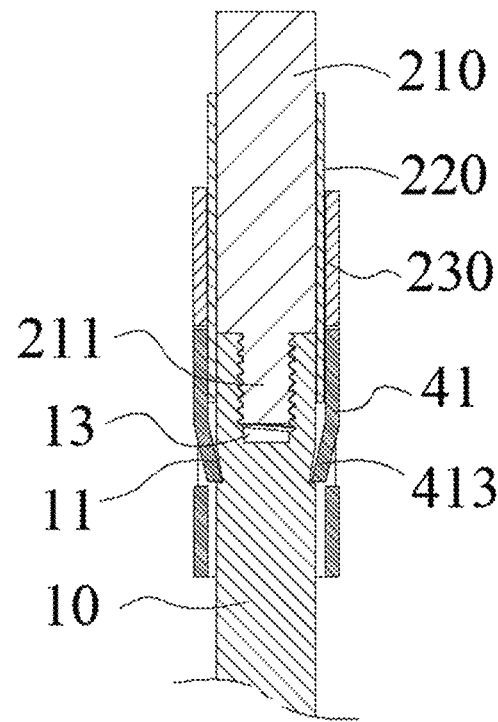
FIG. 18 is a cross sectional view of FIG. 17.

Referring to FIG. 17 and FIG. 18, the application further provides a valve clamping system. The valve clamping system includes a pushing device and the foregoing valve clip 100. Through the pushing device, the valve clip 100 may be delivered to the mitral valve and adjusted to a proper position of the mitral valve. The pushing device includes an operating handle and a pushing component. A proximal end of the pushing component is connected to the operating handle. A distal end of the pushing component is detachably connected to the valve clip 100. In an implementation, the pushing component includes a mandrel 210, a bushing 220, and an outer tube 230 that are movably coaxially mounted in a sleeving manner. The bushing 220 is arranged between the mandrel 210 and the outer tube 230. The operating handle can respectively drive the mandrel 210, the bushing 220, and the outer tube 230 to move relatively.

A distal end of the mandrel 210 is provided with an external thread 211 corresponding to an internal thread in an internal threaded hole 13 at the proximal end of the push rod 10. When the pushing component is connected to the valve clip 100, the distal end of the mandrel 210 and the proximal end of the push rod 10 are in threaded connection. The operating handle drives the mandrel 210 to move so as to drive the push rod 10 to move axially.

A T-shaped elastic piece 231 is arranged at the distal end of the outer tube 230, for cooperating with the connecting part 415 (i.e., the T-shaped slot) at the proximal end of the first base body 41 to achieve connection and disconnection between the outer tube 230 and the first base body 41. In a natural state, one end of the T-shaped elastic piece 231 is connected to the distal end of the outer tube 230, while the other end thereof is inclined toward the axis of the outer tube 230. In an implementation, when the pushing component is connected to the valve clip 100, the mandrel 210 and the push rod 10 are in threaded connection, the operating handle drives the bushing 220 to move, so that the bushing 220 is inserted into the tube cavity of the first base body 41, to jack up the T-shaped elastic piece 231 of the outer tube 230, and then the T-shaped elastic piece 231 is embedded in the T-shaped slot of the first base body 41. Here, the first base body 41 and the outer tube 230 are connected. When the operating handle is operated to drive the bushing 220 to leave the first base body 41, the T-shaped elastic piece of the outer tube 230 restores to a natural state, that is, the T-shaped elastic piece is deformed inwards and separated from the T-shaped slot at the proximal end of the first base body 41, and therefore the first base body 41 and the outer tube 230 are unlocked.

The pushing device further comprises a control member. The control member is the foregoing adjusting wire which is used to restrain the free ends 212 of the proximal clamping plate 21 to the surface of the fixing base 40 to be adjacent to the push rod 10. The adjusting wire may be made of a metal or a polymer material such as PTFE.

The following takes a mitral valve repair process as an example to illustrate an operation method of the valve clamping system of the application, which mainly includes the following steps.

At the first step, the free ends 212 of the proximal clamping plate 21 are restrained on the surface of the fixing base 40 through the adjusting wire, and the pushing component is connected to the valve clip 100. In an implementation, the mandrel 210 of the pushing component is rotated to be fixed to the push rod 10. The bushing 220 is axially moved toward the distal end, so that the T-shaped elastic piece 231 of the outer tube 230 is jacked up to be embedded into the T-shaped groove of the first base body 41, and the first base body 41 and the outer tube 230 are kept in a connection state. In addition, the free end of the elastic piece 413 on the first base body 41 is in the circular groove 11 of the push rod 10, so that both the distal clamping plate 23 and the proximal clamping plate 21 are attached to the surface of the push rod 10 and kept in a constant state.

At the second step, by a way of the interatrial septum, through the pushing component, the valve clip 100 connected thereto is pushed from the left atrium, and enters the left ventricle through the mitral valve.

At the third step, a relative position of the valve clip 100 and the mitral valve is adjusted by the pushing component so that the valve clip 100 approaches the anterior leaflet 1*a* and the posterior leaflet 1*b* of the mitral valve.

At the fourth step, the bushing 220 is further axially moved to the distal end, to lift the free end of the elastic piece 413 of the first base body 41, so that the free end of the elastic piece 413 leaves the circular groove 11 at the proximal end of the push rod 10. Here, the push rod 10 can axially move to drive the distal clamping plate 23 to be unfolded and folded relative to the push rod 10.

At the fifth step, the mandrel 210 is moved toward the proximal end through the operating handle to drive the push rod 10 connected to the mandrel 210 to move toward the proximal end, thereby driving the distal clamping plate 23 to be unfolded and folded relative to the push rod 10. In an implementation, the mandrel 210 is moved toward the proximal end through the operating handle to drive the push rod 10 connected to the mandrel 210 to move toward the proximal end, thereby driving the distal clamping plate 23 to be expanded and contracted relative to the push rod 10.

At the sixth step, a direction of the valve clip 100 is adjusted so that the distal clamping plate 23 is perpendicular to a coaptation line of the mitral valve.

At the seventh step, the valve clip 100 is withdrawn toward the proximal end, so that the distal clamping plate 23 may support the leaflets at one side of the left ventricle. When the proximal clamping plate is released from the adjusting wire, the proximal clamping plate 21 rebounds to be unfolded relative to the push rod 10, and thus, the valve leaflets are clamped between the proximal clamping plate 21 and the distal clamping plate 23, that is, the anterior leaflet 1*a* and the posterior leaflet 1*b* of the mitral valve are respectively clamped in a set of the proximal clamping plate 21 and the distal clamping plate 23.

At the eighth step, the mandrel 210 is moved to the distal end to drive the push rod 10 to axially move toward the distal end, thereby driving the distal clamping plate 23 to be folded relative to the push rod 10 until the distal clamping plate 23 is fully folded or retracted.

At the ninth step, the outer tube 230 is fixed, the bushing 220 is withdraw by a certain stroke toward the proximal end. Here, the free end of the elastic piece 413 of the first base body 41 is clamped in the circular groove 11 of the push rod 10, and thus the push rod 10 is locked to ensure that the distal clamping plate 23 is always folded. The mandrel 210 is controlled to rotate by the operating handle, so that the thread between the mandrel 210 and the push rod 10 is unlocked. The bushing 220 and the mandrel 210 are withdrawn toward the proximal end until the T-shaped elastic piece 231 of the outer tube 230 is unlocked and separated from the T-shaped groove of the first base body 41. At this time, the valve clip 100 is completely separated from the pushing component. The pushing assembly is withdrawn from the patient's body, and the valve clip 100 is remained in the patient's body to complete the edge-to-edge repair of the mitral valve leaflets. As shown in FIG. 14, the proximal clamping plate 21 of the valve clip 100 is fixed on the atrial side of the valve leaflets, and the first coating 31 is in contact with the atrial side of the valve leaflets, which isolates the proximal clamping plate 21 from direct contact with the valve leaflets, increases the friction force of the metal proximal clamping plate 21 on the valve leaflets, uniformizes the stress and the force of each barb, and prevent damage to the valve leaflets due to too deep penetration or uneven force, and excessive force. Moreover, the second coating 32 can improve the adhesion of the distal clamping plate 23 to the valve, and increase the contact area between the distal clamping plate 23 and the valve, and play a buffering role on the surfaces of the distal clamping plate 23 to avoid direction contact between the metal and the valve, thereby reducing the mechanical force on the valve and avoiding inflammation.

It can be understood that the valve clamping system of the application may also use a path such as transapical delivery of the valve clamp to the mitral valve.

The valve clamping system of the application can be operated outside the body to clamp the valve leaflets with the valve clip 100, thereby reducing or avoiding the problem of "mitral valve regurgitation", and the coatings 30 of the valve clip 100 can reduce or avoid damage to the clamped valve tissue, and also avoid damage to the valve tissue or other blood vessel tissues during the pushing process.

Figure 19:
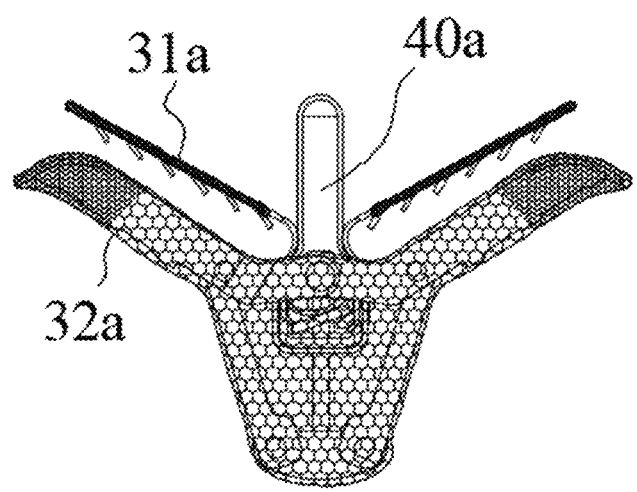
FIG. 19 is a schematic view illustrating a valve clip in an unfolded state according to another implementation of the application.
Figure 20:
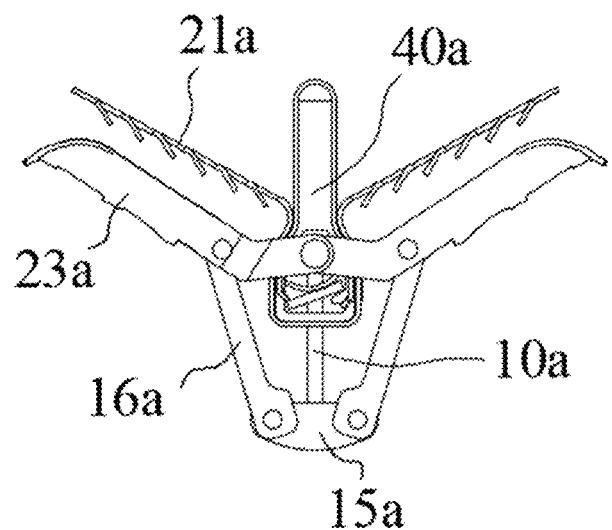
FIG. 20 is a schematic view of the valve clip in FIG. 19 before being covered with coatings.

Referring to FIG. 19 and FIG. 20, a valve clamp 100*a* in another implementation of the application is shown. The valve clamp 100*a* includes a push rod 10*a*, a distal clamping plate 23*a* which are arranged on the outer surface of the push rod 10*a* in axial symmetry and may be unfolded and folded relative to the push rod 10*a*, a proximal clamping plate 21*a* matching with the distal clamping plate 23*a* to clamp and fix the leaflets, a first coating 31*a* covering the proximal clamping plate 21*a*, and a second coating 32*a* covering the distal clamping plate 23*a*. When the distal clamping plate 23*a* is folded relative to the push rod 10*a*, the valve clip may be delivered to near the patient's valve through a sheath. Structures of the proximal clamping plate 21*a* and the first coating 31*a* are the same as those of the proximal clamping plate 21 and the first coating 31 of the valve clip 100 in the first implementation, and which will not be elaborated here.

Figure 21:
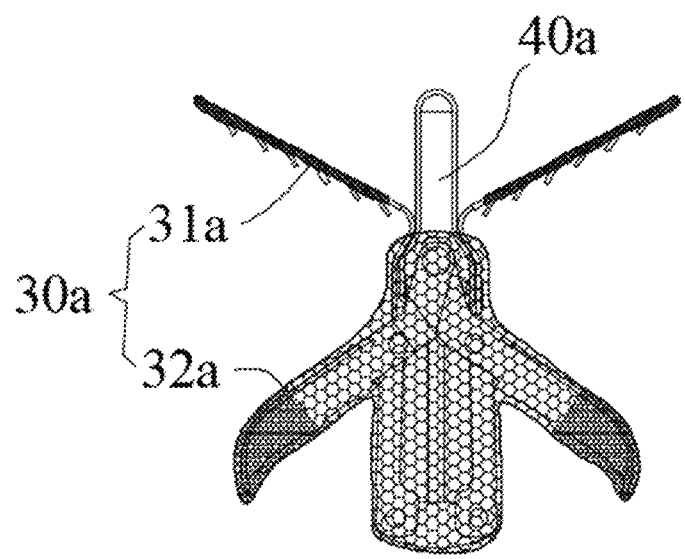
FIG. 21 is a schematic view illustrating a distal clamping plate in a turnover state of the valve clip in FIG. 19.

A connecting base 15*a* is located at the distal end of the push rod 10*a*, The proximal end of the connecting base 15*a* defines a round hole therein for connecting the push rod 10*a* by means of such as threads, and welding. Pin holes are defined on both sides of the connecting base 15*a*. A pair of connecting rods 16*a* are connected through a pin hinge, that is, each connecting rod 16*a* is connected to the connecting base 15*a* through a hinge so as to rotate relative to same. The other end of the connecting rod 16*a* is connected to the distal clamping plate 23*a* by a pin. A fixing base 40*a* sleeves the outside of the push rod 10*a*, and the push rod 10*a* may move along its axial direction, so that movement between the connecting base 15*a* and the fixing base 40*a* is realized, to further drive the distal clamping plate 23*a* to open and close relative to the push rod 10*a*. Referring to FIG. 21, in this way, a wide range of angle opening may be achieved, and the angle between the two distal clamping plates 23*a* may reach a maximum of 320 degrees, preferably the opening angle ranges from 0 degrees to 270 degrees, and further preferably ranges from 120 degrees to 180 degrees. That is, after the distal clamping plate 23*a* is opened relative to the push rod 10*a*, they may be turned downward to a certain extent. Due to elastic retraction functions of the second coating 32a, when the distal clamping plate 23a is opened, the second coating 32a can correspondingly deform without obvious resistance, thereby facilitating the clamping of the valve leaflets that are constantly in motion, and increasing the clamping success rate.

Figure 22:
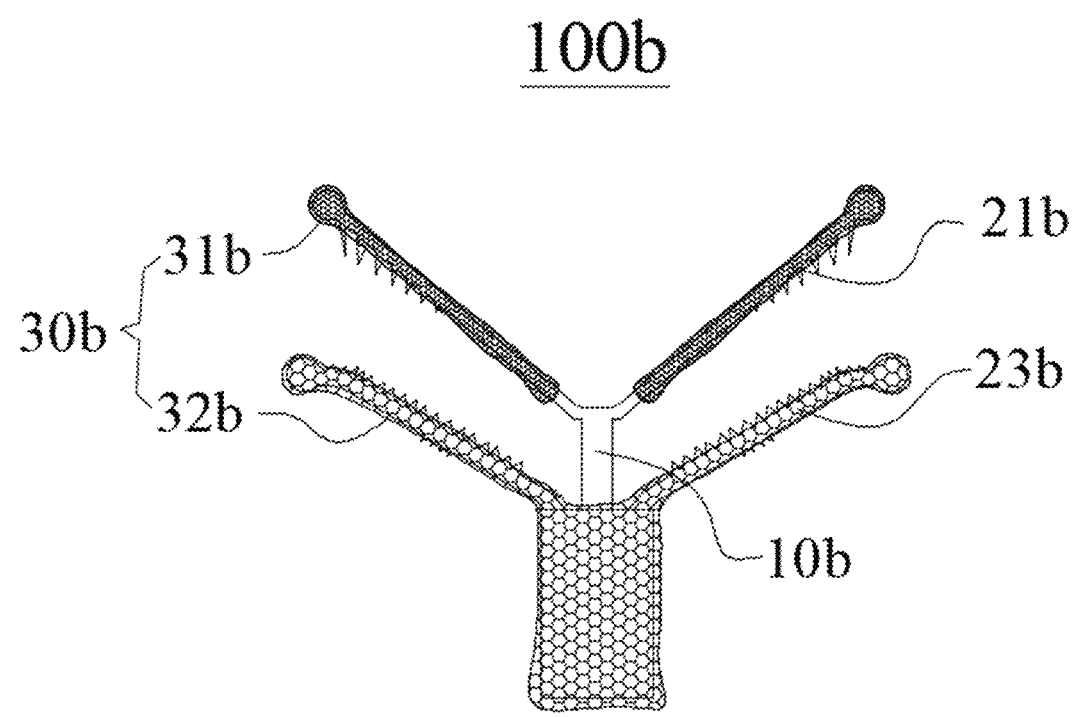
FIG. 22 is a schematic view illustrating a valve clip in an unfolded state according to another implementation of the application.

FIG. 22 shows a valve clip 100b provided in another implementation of the application. The difference between this implementation and the implementation shown in FIG. 3 lies in that the valve clip 100b includes a V-shaped proximal clamping plate 21b and a V-shaped distal clamping plate 23b. A push rod 10b drives the proximal clamping plate 21b and the distal clamping plate 23b to do relative movement and folding to clamp the two leaflets.

At least a part of a side face, facing the distal clamping plate 23b, of the proximal clamping plate 21b, and a part of a side surface, facing the proximal clamping plate 21b, of the distal clamping plate 23b are covered with coatings 30b.

In an implementation, each proximal clamping plate 21b is covered with a first coating 31b. The distal clamping plate 23b is covered with a second coating 32b. The jointed part between the two distal clamping plates 23b is covered together with the second coating 32b.

It can be understood that a jointed part between the two proximal clamping plates 21b may also be covered with the first coating 31b.

The first coating 31b and the second coating 32b have the same structure and function as the foregoing first coating 31 and the second coverings 32, which will not be elaborated herein.

It can be understood that the valve clips 100a and 100b and the pushing device can also form a valve clamping system, and the usage steps are the same as the foregoing content, which will not be elaborated here.

It should be noted that the above content is described with the valve clip 100 being used for alleviating or treating "mitral valve regurgitation" as an example. It can be understood that in other implementations, the valve clip 100 can also be used to alleviate or treat "tricuspid valve regurgitation", and its principle and structure are substantially the same as those used in the implementations of the application to solve "mitral valve regurgitation". That is, multiple clamps are formed by multiple sets of proximal clamping plates and distal clamping plate respectively, and each clamp may clamp a leaflet separately, which will not be elaborated here.

It is apparent that in other implementations, the valve clip 100 provided in the application can also be applied to other minimally invasive surgical operations that require more than three flap-shaped valve tissues to be clamped together.

The above is the implementation manners of the implementations of the application. It should be pointed out that those of ordinary skill in the art may also make several improvements and modifications without departing from the principle of the implementations of the application. These improvements and modifications shall fall within the scope of protection of the application.

What is claimed is:

1. A valve clip with coatings, comprising:
    a push rod;
    a proximal clamping plate and a distal clamping plate extending radially outwardly relative to the push rod, wherein
        the distal clamping plate is connected to the push rod,
        the proximal clamping plate is arranged between the push rod and the distal clamping plate,
        a valve holding space is formed between the proximal clamping plate and the distal clamping plate,
        the push rod is capable of driving the distal clamping plate to be expanded radially, and
        the proximal clamping plate is capable of expanding toward the distal clamping plate by an elastic strain of the proximal clamping plate and is configured to clamp a valve tissue received in the valve holding space; and
    the coatings comprising a first coating and a second coating, wherein
        the first coating covers at least one side, facing the valve holding space, of the proximal clamping plate,
        the second coating covers at least one side, facing the valve holding space, of the distal clamping plate,
        each of the first coating and the second coating is a mesh structure, a porosity of the first coating is less than that of the second coating,
        a diameter of each of meshes of the first coating is less than that of each of meshes of the second coating, and
        diameters of the meshes arranged, along a direction from a proximal end to a distal end of the distal clamping plate, of the second coating are gradually increased.

2. The valve clip of claim 1, wherein the proximal clamping plate is made of an elastic material having a shape memory function.

3. The valve clip of claim 2, wherein the distal clamping plate is made of a rigid material.

4. The valve clip of claim 2, wherein when the proximal clamping plate is free of external force, the proximal clamping plate has an opening angle greater than a maximum angle of the distal clamping plate.

5. The valve clip of claim 1, wherein a coverage rate of the first coating on the proximal clamping plate ranges from 50% to 90%, a coverage rate of the second coating on the distal clamping plate ranges from 40% to 80%.

6. The valve clip of claim 1, wherein the first coating extends and covers edges of the proximal clamping plate, the second coating extends and covers edges of the distal clamping plate.

7. The valve clip of claim 1, wherein the proximal clamping plate comprises a first surface facing the distal clamping plate, the first coating at least partially covers the first surface.

8. The valve clip of claim 7, wherein the proximal clamping plate further comprises a second surface opposing the first surface, and the first coating covers at least part of the second surface.

9. The valve clip of claim 7, wherein the first surface is provided with at least one barb, a free end of the at least one barb faces the distal clamping plate, and the at least one barb penetrates out of the first coating.

10. The valve clip of claim 9, wherein the free end of the at least one barb penetrates out of the first coating by a length ranging from 0.2 mm to 2 mm.

11. The valve clip of claim 9, wherein a thickness of a region of the first coating close to the at least one barb is greater than that of other regions of the first coating covering the proximal clamping plate.

12. The valve clip of claim 1, wherein the distal clamping plate comprises a third surface facing the proximal clamping plate, the second coating at least covers the entire third surface.

13. The valve clip of claim 12, wherein the distal clamping plate further comprises a fourth surface opposing the third surface, the second coating covers at least part of the fourth surface.

14. A valve clamping system, comprising a pushing device and a valve clip with coatings, wherein:
the pushing device comprises an operating handle and a pushing component, a proximal end of the pushing component is connected to the operating handle, and a distal end of the pushing component is detachably connected to the valve clip; and
the valve clip comprises:
a proximal clamping plate and a distal clamping plate extending radially outwardly relative to a push rod, wherein the distal clamping plate is connected to the push rod, the proximal clamping plate is arranged between the push rod and the distal clamping plate, a valve holding space is formed between the proximal clamping plate and the distal clamping plate, the push rod is capable of driving the distal clamping plate to be expanded radially, and the proximal clamping plate is capable of expanding toward the distal clamping plate by an elastic strain of the proximal clamping plate and is configured to clamp a valve tissue received in the valve holding space; and
the coatings comprising a first coating and a second coating, wherein
the first coating covers at least one side, facing the valve holding space, of the proximal clamping plate,
the second coating covers at least one side, facing the valve holding space, of the distal clamping plate,
each of the first coating and the second coating is a mesh structure, a porosity of the first coating is less than that of the second coating,
a diameter of each of meshes of the first coating is less than that of each of meshes of the second coating, and
diameters of the meshes arranged, along a direction from a proximal end to a distal end of the distal clamping plate, of the second coating are gradually increased.

15. The valve clamping system of claim 14, wherein the pushing component comprises a mandrel, a bushing, and an outer tube that are movably coaxially mounted in a sleeving manner, and the bushing is arranged between the mandrel and the outer tube.

16. The valve clamping system of claim 14, wherein the pushing device further comprises a control member configured to fix the proximal clamping plate so that the proximal clamping plate fit the push rod.

17. The valve clamping system of claim 14, wherein when the proximal clamping plate is free of external force, the proximal clamping plate has an opening angle greater than a maximum angle of the distal clamping plate.

* * * * *